United States Patent [19]
Thompson

[11] Patent Number: 5,551,090
[45] Date of Patent: Sep. 3, 1996

[54] EAR PROTECTING APPARATUS

[76] Inventor: Janet M. Thompson, 3211 Travelers Palm Dr., Edgewater, Fla. 32141

[21] Appl. No.: 425,927

[22] Filed: Apr. 20, 1995

[51] Int. Cl.⁶ ............................. A01F 11/02; G10K 11/04
[52] U.S. Cl. ............................. 2/209; 181/129; 128/866; 128/867
[58] Field of Search ...................... 2/209, 423, 6.3, 2/6.7; 181/175, 129; 128/866, 867

[56] References Cited

U.S. PATENT DOCUMENTS

| | | | |
|---|---|---|---|
| 437,602 | 9/1890 | Kaiser | 2/209 |
| 1,225,422 | 5/1917 | Feher | 2/209 U X |
| 2,738,514 | 3/1956 | Gondell | 2/209 |
| 3,506,981 | 4/1970 | Stewart et al. | 2/209 |
| 4,023,642 | 5/1977 | Korn | 2/209 |
| 4,459,707 | 7/1984 | Stallings | 2/209 |
| 4,471,496 | 9/1984 | Gardner, Jr. et al. | 2/209 |
| 4,928,311 | 5/1990 | Trompier | 381/72 |
| 4,944,361 | 7/1990 | Lindgren et al. | 181/129 |
| 5,243,709 | 9/1993 | Sheehan et al. | 2/209 |

*Primary Examiner*—Peter Nerbun
*Attorney, Agent, or Firm*—Weiner, Carrier & Burt, P.C.; Pamela S. Burt; Irving M. Weiner

[57] ABSTRACT

An ear protecting apparatus adapted to protect children and infants from discomfort and potential hearing damage associated with noisy environments. The apparatus includes an adjustable headband having a pair of noise-attenuating earmuffs provided at opposite ends thereof, respectively. Each earmuff includes an annular member which entirely surrounds the user's ear and a noise-attenuating dome-shaped member which is shaped, dimensioned, and adapted to press against an outer portion of the user's auditory canal to effectively seal same from loud noise. Both the annular member and the dome-shaped member are preferably fabricated of a noise-attenuating foam material. The headband is spring-biased to urge the earmuffs inwardly so that they will be comfortably pressed into position on and around the user's ears.

11 Claims, 1 Drawing Sheet

EAR PROTECTING APPARATUS

BACKGROUND OF THE INVENTION

1. Field of the Invention

The present invention relates generally to an ear protecting apparatus which attenuates loud noises so as to protect against discomfort and/or hearing loss. More particularly, the invention relates to a noise-attenuating earmuff apparatus which is particularly constructed and dimensioned to fit children and infants. Further, the invention comprises a pair of noise-attenuating members which are shaped and dimensioned to be pressed against the outer end portions of the auditory canals of the user's ears.

2. Description of the Relevant Art

It is known that prolonged exposure to sound above substantially 85 decibels can cause hearing damage, while sound levels at motor sports events such as drag races typically rise to well over 110 decibels. Children are particularly vulnerable to hearing damage in such excessively noisy environments. Because the human pain threshold for sound is not reached until well after the danger of hearing damage has become acute, hearing damage can occur before sounds become painful to the ear.

Various different types of protective earmuff devices are known for attenuating noise in environments where the noise level is high and potentially damaging. Exemplary acoustic earmuff devices are disclosed in the following United States patents: U.S. Pat. No. 3,506,981 issued Apr. 21, 1970 to Stewart et al entitled "Noise Absorbing Earmuffs"; U.S. Pat. No. 4,459,707 issued Jul. 17, 1984 to Stallings entitled "Ear Protecting Device"; U.S. Pat. No. 4,928,311 issued May 22, 1990 to Trompler entitled "Noise Limiting Circuit for Earmuffs; and U.S. Pat. No. 4,944,361 issued Jul. 31, 1990 to Lindgren et al entitled "Acoustic Ear Muff".

A principal limitation associated with the above known protective earmuff devices is that they are sized and constructed to be worn by adults, so that they do not effectively or comfortably fit the heads and ears of children and infants. While U.S. Pat. No. 5,243,709 issued Sep. 14, 1993 to Sheehan et al discloses an "Acoustically Sealing Earmuff for an Infant", the device is constructed and dimensioned to fit a neonatal infant and requires the use of hydrogel adhesive to secure the individual earmuffs against the infant's head.

There has thus developed a desideratum for an effective noise-attenuating earmuff device for use by children so as to protect them from loud noises. Exemplary environments in which children are exposed to uncomfortable and/or damaging loud noises include motor sports events such as drag races, monster truck shows, tractor pulls, Nascar races, and the like.

The present invention overcomes the disadvantages of known ear protecting devices and fulfills the aforesaid desideratum by providing a noise-attenuating earmuff apparatus which is particularly constructed and dimensioned to comfortably and effectively fit the heads and ears of children and infants.

In contrast to known protective earmuff devices, the invention further provides a novel noise-attenuating earmuff apparatus comprising a noise-attenuating member adapted to be positioned within, and to be pressed against, the opening in the ear defined by the outer end portions of the auditory canal.

SUMMARY OF THE INVENTION

The invention provides an ear protecting apparatus for children and infants, comprising a pair of ear protecting earmuffs and an adjustable headband having the ear protecting earmuffs provided at opposite ends thereof, respectively. Each ear protecting earmuff includes a first predetermined noise-attenuating annular member which completely surrounds an ear of the user of the apparatus to hold the apparatus in place. Each ear protecting earmuff further includes a second predetermined noise-attenuating dome-shaped member which is shaped, dimensioned, and adapted to press against an outer end portion of the auditory canal of the ear of the user to substantially seal the auditory canal from sound.

In a preferred embodiment, the headband and the ear protecting earmuffs are dimensioned to fit a child or infant. The annular member and the dome-shaped member of each earmuff is fabricated of a foam material.

It is an object of the invention to provide a noise-attenuating earmuff apparatus for children and infants to protect them from the discomfort and potential hearing damage associated with noisy environments.

A further object of the invention is to provide a noise-attenuating earmuff which comfortably and effectively seals the ears from loud noises, such as those associated with motor sports events.

The above and further objects, details and advantages of the invention will become apparent from the following detailed description, when read in conjunction with the accompanying drawings.

DETAILED DESCRIPTION OF PREFERRED EMBODIMENTS

Figure 1:
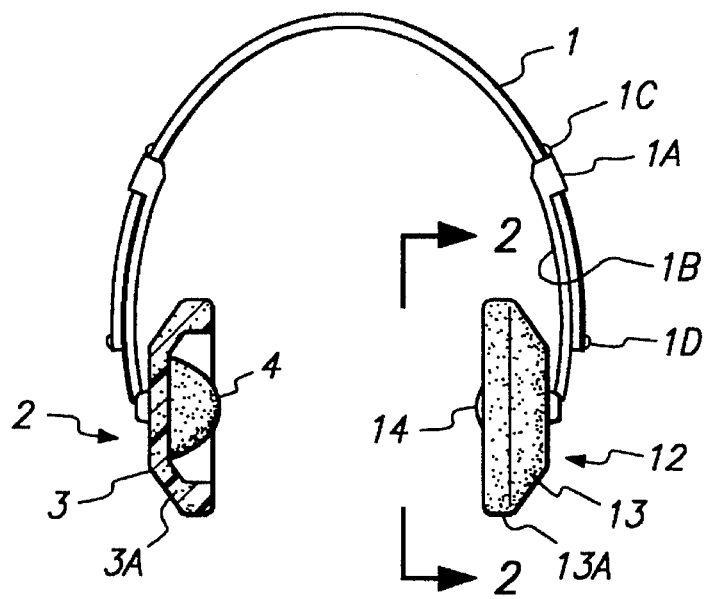
FIG. 1 is a front view, partially cut-away, of an ear protecting apparatus according to a preferred embodiment of the invention.
Figure 2:
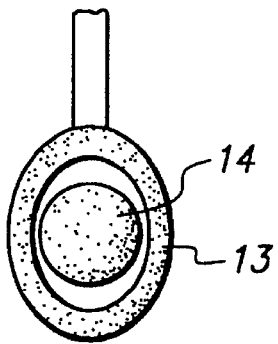
FIG. 2 is a side elevational view taken along line 2—2 in FIG. 1.
Figure 3:
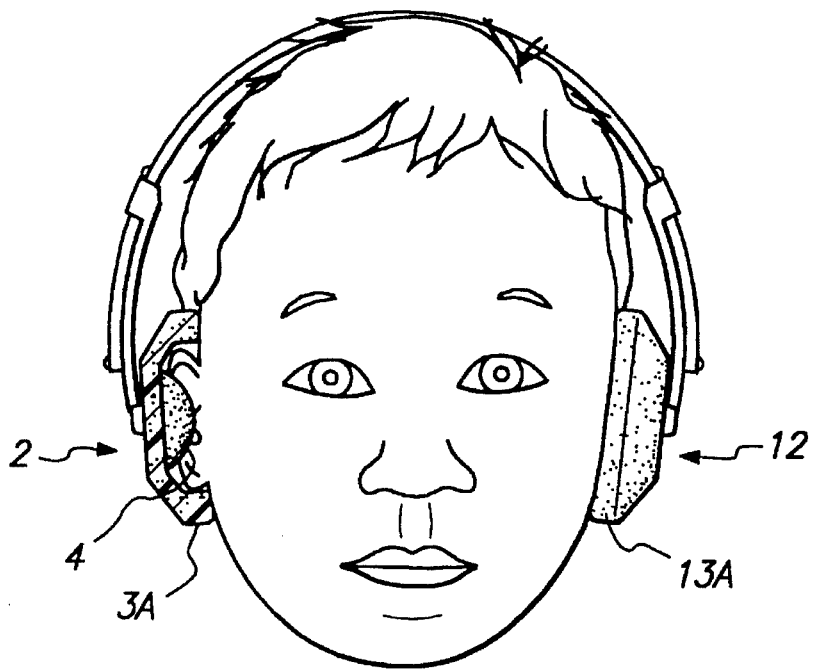
FIG. 3 is a view of the ear protecting apparatus according to the invention, partially cut-away, being worn by a child.

With reference to FIGS. 1 and 2 showing a preferred embodiment of the invention, the ear protecting apparatus according to the invention generally takes the form of a noise-attenuating earmuff apparatus. A pair of earmuffs 2, 12 are respectively mounted on the opposite ends of a headband 1. The headband 1 is preferably adjustable as shown in FIG. 1, and to this end includes a pair of slides 1A each having a headband extension 1B extending therefrom. The slide 1A is snugly received over the main body of headband 1 so as to remain in an adjusted position until firm pressure is applied thereto so as to slide same along headband 1. The slide 1A is slidable between a first dimple 1C and a second dimple 1D provided on headband 1, thus permitting substantial adjustability of the size of headband 1. It will be understood, however, that the adjustment mechanism thus defined by components 1A–1D is merely exemplary, while the invention contemplates that any suitable adjustment mechanism for headband 1 can be employed as desired. Alternatively, as shown in FIG. 3, the headband 1 can be fixed in size without an adjustment mechanism.

The noise-attenuating earmuffs 2, 12 are substantially identical in construction, with each comprising an outer cup-shaped member 3, 13 having an annular member 3A, 13A, respectively, extending integrally therefrom. Extending inwardly from central inner wall portions of cup members 3, 13 are dome-shaped members 4, 14, respectively.

The dome-shaped members 4, 14 are constructed of a noise-attenuating foam material, such as foam rubber, neoprene, or any other suitable material having noise-attenuating properties and sufficient resiliency as to be comfortably pressed against the user's ear. Each dome-shaped member 4, 14 is shaped and dimensioned to be pressed against the outer end portion of the user's auditory canal so as to seal same against sound.

The annular members 3A, 13A are also preferably fabricated of a noise-attenuating foam material. To this end, the cup-shaped members 3, 13 from which annular members 3A, 13A extend may be integrally formed of the same foam material as the annular members, or alternatively made be fabricated of a more rigid material such as plastic or the like. Each annular member 3A, 13A is shaped and dimensioned to closely and completely surround the user's ear while contacting portions of the user's head and face, as shown in FIG. 3.

To ensure that the earmuffs are substantially firmly pressed into position around and on the user's ears, the headband 1 has a spring-like construction by virtue of which the respective ends supporting earmuffs 2, 12 are spring-biased inwardly towards the user's head. To this end, the headband 1 may be constructed of a suitable metal or plastic material which is formed such that earmuffs 2 and 12 are normally biased substantially together so that they must be pulled away from each other to fit the apparatus on the user's head. The spring-biasing force of headband 1 is selected such that the dome-shaped members 4, 14 will be firmly but comfortably pressed against the outer ends of the auditory canals, while the annular members 3A, 13A are firmly but comfortably pressed against the user's face and head around the ears.

The invention contemplates that in order to achieve the desired firm but comfortable pressing of the earmuffs in their proper position, the spring force of the headband as well as the relative stiffness or resiliency of the foam material from which dome-shaped members 4, 14 and annular members 3A, 13A are fabricated are both selected to achieve the desired final fit. When the apparatus is in an operative position on a user's head, as shown in FIG. 3, pressing of the dome-shaped members 4, 14 against the openings of the auditory canal will operatively cooperate with pressing of the annular members 3A, 13A against the face and head around the ears so as to aid in keeping the earmuffs 2, 12 in their proper positions.

In a preferred embodiment of the invention, the construction and dimensions of the apparatus are particularly adapted to fit children and/or infants. To this end, the headband 1 as well as the components of earmuffs 2, 12 are substantially smaller than commercially-available protective earmuffs which are designed to fit adults. It is further contemplated that the apparatus may be provided in a range of sizes so as to accommodate newborn infants, toddlers, older children, and adults, as desired.

For safety reasons, it is preferable that the entire apparatus be constructed without any sharp edges or protrusions. In addition, to heighten the attractiveness of the apparatus to children, various components of the apparatus may be brightly colored. If desired, appliques, insignia, or molded pieces representing popular cartoon characters or the like may be added, as desired.

It will be understood from the foregoing that the ear protecting apparatus according to the invention provides an effective means for protecting infants and children from hearing damage and/or discomfort associated with very noisy environments, such as motor sports events. The invention further contemplates that, if desired, the apparatus may be constructed and dimensioned to fit adults.

While there have been described above what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

I claim:

1. An ear protecting apparatus for children and infants, comprising:

a pair of ear protecting earmuffs;

a headband having said ear protecting earmuffs provided at opposite ends thereof, respectively;

each said ear protecting earmuff including a first predetermined noise-attenuating annular member which closely and completely surrounds an ear of the user of said apparatus;

each said ear protecting earmuff further including a second predetermined noise-attenuating member, said second member being dome shaped and having a substantially smooth, rounded surface which in an operative position presses against the opening of the auditory canal of said ear of said user, without protruding into said auditory canal, to substantially seal said auditory canal from sound;

said headband having a spring-like construction so as to apply a biasing force to each of said annular members and dome-shaped members such that said members are substantially firmly biased inwardly towards the user's head;

each said inwardly-biased annular member and respective dome-shaped member of each said earmuff operatively cooperating so as to retain said earmuff in position around said ear of said user; and said headband and said ear protecting earmuffs being dimensioned to fit a child or infant.

2. An ear protecting apparatus according to claim 1, wherein:

each said ear protecting earmuff comprises a cup-shaped member having said annular member extending integrally therefrom; and said dome-shaped member extends from an inner wall of said cup-shaped member.

3. An ear protecting earmuff apparatus according to claim 1, wherein:

said first predetermined noise-attenuating annular member is made from foam material.

4. An ear protecting earmuff apparatus according to claim 1, wherein:

said second predetermined noise-attenuating dome-shaped member is made from foam material.

5. An ear protecting earmuff apparatus according to claim 3, wherein:

said second predetermined noise-attenuating dome-shaped member is made from foam material.

6. A noise-attenuating earmuff apparatus according to claim 1, wherein:

said headband is adjustable.

7. A noise-attenuating earmuff apparatus for children and infants, comprising:

a pair of noise-attenuating earmuffs;

a headband device interconnecting said earmuffs;

each said earmuff comprising a cup-shaped member having a first predetermined noise-attenuating annular member extending therefrom, said annular member substantially closely and completely surrounding an ear of a user of said apparatus; and each said earmuff device further including a second predetermined noise-attenuating member, said second member being dome-shaped and extending from said cup-shaped member, said dome-shaped member having a completely smoothly-rounded shape, said dome-shaped member pressing against the opening of the auditory canal of said ear of said user, without protruding into said auditory canal;

said headband device being constructed so as to apply a biasing force to each of said annular members and dome-shaped members such that said members are substantially firmly biased inwardly towards the user's head;

each said inwardly-biased annular member and respective dome-shaped member of each said earmuff defining an annular channel therebetween which in an operative position of said apparatus closely receives an ear of said user.

8. A noise-attenuating earmuff apparatus according to claim 7, wherein:

said headband device is adjustable.

9. A noise-attenuating earmuff apparatus according to claim 7, wherein:

said annular member is made from foam material.

10. A noise-attenuating earmuff apparatus according to claim 7, wherein:

said dome-shaped member is made from foam material.

11. A noise-attenuating earmuff apparatus according to claim 19, wherein:

said annular member is made from foam material; and said dome-shaped member is made from foam material.

* * * * *